(12) United States Patent
Jennings et al.

(10) Patent No.: US 9,737,663 B2
(45) Date of Patent: Aug. 22, 2017

(54) AUTO-INJECTOR

(75) Inventors: Douglas Jennings, Herts (GB); Thomas Kemp, Hertfordshire (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 886 days.

(21) Appl. No.: 13/994,885

(22) PCT Filed: Dec. 21, 2011

(86) PCT No.: PCT/EP2011/073512
§ 371 (c)(1),
(2), (4) Date: Jun. 17, 2013

(87) PCT Pub. No.: WO2012/085030
PCT Pub. Date: Jun. 28, 2012

(65) Prior Publication Data
US 2013/0281929 A1 Oct. 24, 2013

Related U.S. Application Data

(60) Provisional application No. 61/432,237, filed on Jan. 13, 2011.

(30) Foreign Application Priority Data

Dec. 21, 2010 (EP) .................................. 10196076

(51) Int. Cl.
*A61M 5/20* (2006.01)
*A61M 5/24* (2006.01)
(Continued)

(52) U.S. Cl.
CPC ............ *A61M 5/2033* (2013.01); *A61M 5/20* (2013.01); *A61M 5/24* (2013.01); *A61M 5/1413* (2013.01);
(Continued)

(58) Field of Classification Search
CPC .............. A61M 5/2053; A61M 5/3204; A61M 2005/206; A61M 5/46; A61M 2005/208;
(Continued)

(56) References Cited

U.S. PATENT DOCUMENTS 4,833,384 A * 5/1989 Munro ................ A61M 5/1452
128/DIG. 1
5,305,984 A 4/1994 Chen
(Continued)

FOREIGN PATENT DOCUMENTS

GB 2463034 3/2010
JP 2001/513371 9/2001
(Continued)

OTHER PUBLICATIONS

International Search Report for Int. App. No. PCT/EP2011/073512, completed Jun. 6, 2012.
(Continued)

*Primary Examiner* — Bhisma Mehta
*Assistant Examiner* — Hamza Darb
(74) *Attorney, Agent, or Firm* — Fish & Richardson P.C.

(57) ABSTRACT

The invention relates to a compression connection means for an auto-injector (A), wherein the compression connection means adapted to attach a front-end device of the auto-injector (A) to a back-end device of the auto-injector (A) comprises of an annular mounting sleeve that is axially displaceable parallel to a longitudinal axis (X) between a locked position (L) and an unlocked position, a mounting sleeve spring biasing the mounting sleeve towards a locked position (L), at least one latch arm connected to one of either the front-end device or the back-end device, wherein the latch arm is deflectable in a radial direction, wherein the mounting sleeve in the locked position (L) is arranged to prevent the radial deflection of the latch arm and wherein the
(Continued)

mounting sleeve in the unlocked position allows for a radial deflection of the latch arm, so as to allow the latch arm to be deflected on assembly or disassembly of the front-end device to the back-end device and to latch to or unlatch from the other of the front-end device or the back-end device.

9 Claims, 9 Drawing Sheets

(51) Int. Cl.
    *A61M 5/14*     (2006.01)
    *A61M 5/46*     (2006.01)
(52) U.S. Cl.
    CPC .......... *A61M 5/46* (2013.01); *A61M 2205/52* (2013.01); *A61M 2205/6018* (2013.01); *A61M 2205/6054* (2013.01); *A61M 2205/6072* (2013.01)
(58) Field of Classification Search
    CPC ............... A61M 5/326; A61M 5/3213; A61M 2005/31588; A61M 2205/6054; A61M 2205/6072; A61M 2205/52; A61M 2205/6318; A61M 2005/2073
    See application file for complete search history.

(56) References Cited

U.S. PATENT DOCUMENTS

| | | | |
|---|---|---|---|
| 5,599,309 A | 2/1997 | Marshall et al. | |
| 6,171,276 B1* | 1/2001 | Lippe | A61M 5/20 128/DIG. 1 |
| 2002/0095120 A1 | 7/2002 | Larsen et al. | |
| 2004/0215151 A1* | 10/2004 | Marshall | A61M 5/2033 604/198 |
| 2009/0088688 A1* | 4/2009 | Timothy Donald | A61M 5/2033 604/136 |
| 2011/0004165 A1* | 1/2011 | Iio | A61M 5/20 604/197 |
| 2012/0041368 A1* | 2/2012 | Karlsson | A61M 5/3272 604/111 |

FOREIGN PATENT DOCUMENTS

| | | |
|---|---|---|
| JP | 2007/111518 | 5/2007 |
| JP | 2009/521998 | 6/2009 |
| JP | 2009/533124 | 9/2009 |
| WO | 2008/105951 | 9/2008 |
| WO | WO2008/105951 | 9/2008 |
| WO | 2009/141650 | 11/2009 |
| WO | WO2009/141650 | 11/2009 |
| WO | WO 2010/104779 | 9/2010 |
| WO | 2010/125400 | 11/2010 |
| WO | WO2010/125400 | 11/2010 |

OTHER PUBLICATIONS

Japanese Office Action in Japanese Application No. 2013-545338, mailed Nov. 10, 2015, 10 pages.
Japanese Office Action in Japanese Application No. 2013-545338, mailed Sep. 27, 2016, 6 pages.
International Search Report and Written Opinion in International Application No. PCT/EP2011/073512, mailed Jun. 15, 2012, 9 pages.
International Preliminary Report on Patentability in International Application No. PCT/EP2011/073512, dated Jun. 25, 2013, 6 pages.

* cited by examiner

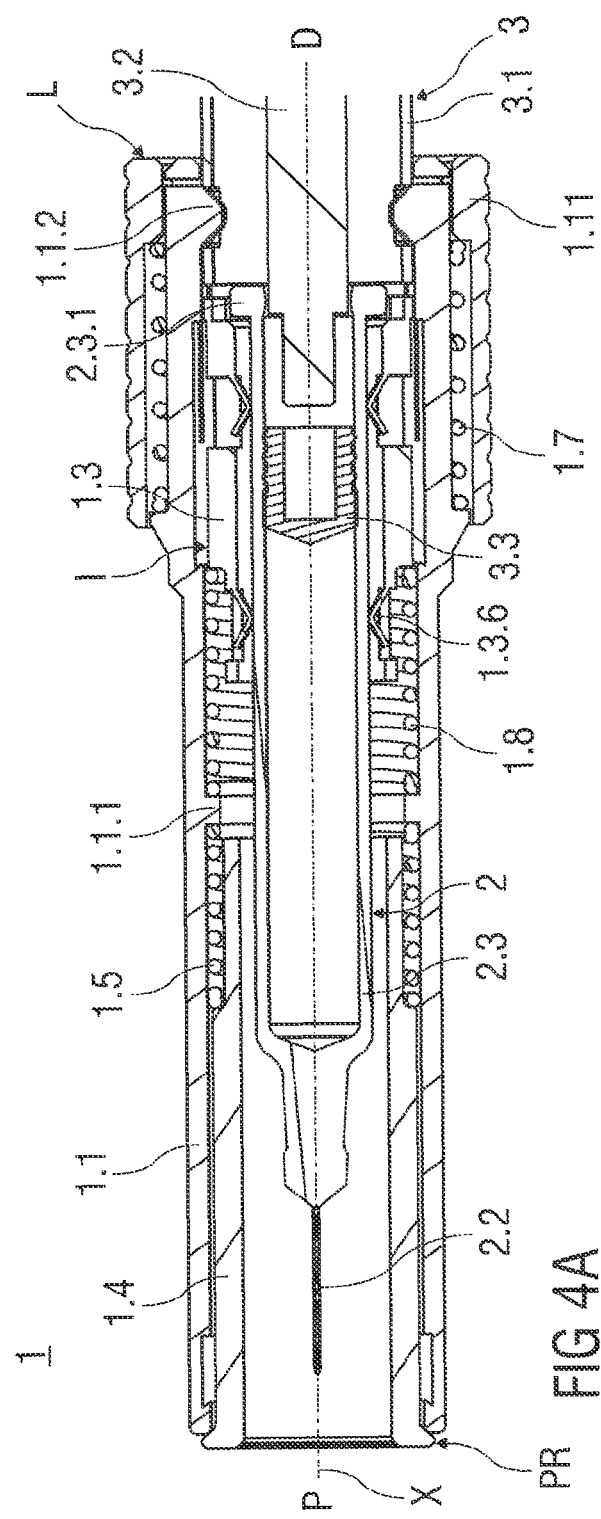

AUTO-INJECTOR

CROSS REFERENCE TO RELATED APPLICATIONS

The present application is a U.S. National Phase Application pursuant to 35 U.S.C. §371 of International Application No. PCT/EP2011/073512 filed Dec. 21, 2011, which claims priority to European Patent Application No. 10196076.3 filed Dec. 21, 2010 and U.S. Provisional Patent Application No. 61/432,237 filed Jan. 13, 2011. The entire disclosure contents of these applications are herewith incorporated by reference into the present application.

TECHNICAL FIELD

The invention relates to a compression connection means for an auto-injector, wherein the compression connection means is adapted to attach a front-end device of the auto-injector to a back-end device of the auto-injector.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button / plunger that has to be continuously pressed by the user during the injection. There are numerous disadvantages to the user from this approach. If the user stops pressing the button / plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling / shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc. Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces / button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved means for releasably connecting a front-end device of an auto-injector adapted to receive a syringe with an injection needle and a barrel containing the dose of the medicament to a back-end device comprising drive means for advancing the syringe for needle insertion and for delivering the medicament.

The object is achieved by a compression connection means according to claim 1.

Preferred embodiments of the invention are given in the dependent claims.

In the context of this specification the term proximal refers to the direction pointing towards the patient during an injection while the term distal refers to the opposite direction pointing away from the patient. The terms "clockwise" and "counter-clockwise" in the context of this specification refer to senses of rotation with the auto-injector pointing with its distal end towards the observer.

According to the invention a front-end device and a back end device of an auto-injector may be releasably connected by a compression connection means comprising
- an annular mounting sleeve that is axially displaceable parallel to a longitudinal axis between a locked position and an unlocked position,
- a mounting sleeve spring biasing the mounting sleeve towards a locked position,
- at least one latch arm connected to one of either the front-end device or the back-end device.

The latch arm is deflectable in a radial direction, wherein the mounting sleeve in the locked position is arranged to prevent the radial deflection of the latch arm and wherein the mounting sleeve in the unlocked position allows for a radial deflection of the latch arm, so as to allow the latch arm to be deflected on assembly or disassembly of the front-end device to the back-end device and to latch to or unlatch from the other of the front-end device or the back-end device.

The compression connection means may be applied with a front-end device of an auto-injector for administering a dose of a liquid medicament. The front-end device is adapted to receive a pre-filled syringe with an injection needle and a barrel containing the dose of the medicament and comprises a tubular outer sleeve and the compression connection means.

A syringe retainer adapted to receive the pre-filled syringe may be slidably arranged with respect to the outer sleeve. The syringe retainer is arranged to be translated between a first position with the needle hidden inside the outer sleeve and a second position with the needle protruding proximally from the outer sleeve. The syringe retainer may comprise at least one flexible arm arranged to latch to the outer sleeve to releasably retain the syringe retainer in the first position.

A needle shroud adapted to rest on the skin of a patient may be slidably arranged with respect to the outer sleeve. The needle shroud is arranged to be translated between an advanced position and a retracted position. The needle shroud comprises an extension arm that is arranged to engage a release ramp on the syringe retainer to de-latch the syringe retainer from the outer sleeve when the needle shroud is in the retracted position. In particular, the needle shroud may be arranged to be pushed against the skin to axially translate the needle shroud into the retracted position. The extension arm may be adapted to communicate the axial displacement of the needle shroud to the back-end device of the auto-injector and thus indicates the back-end device if the auto-injector is properly placed onto the skin of the patient. The back-end device may have means to prevent an activation of an injection mechanism if the needle shield is not positioned in the retracted position and thus is not in contact with the skin of the patient. Therefore, a premature or inadvertent activation of the injection mechanism wasting the medicament and/or compromising safety is avoided.

The front-end device may be part of an auto-injector for administering a dose of a liquid medicament, comprising a reusable back-end device comprising:

a housing, a plunger connected to or adapted to engage a stopper providing a fluid tight seal for a distal end of the syringe barrel, a motor for displacing the plunger connected to the stopper.

The front-end device is attachable to the back-end device via the compression connection means.

A tubular cover may be connected to a needle cap covering the injection needle of the syringe, wherein the tubular cover is arranged to facilitate removal of the needle cap when the syringe is retained within the front-end device.

Before the injection is performed, a pre-filled syringe is loaded into the front-end device. The front-end device is then attached to the back-end device via the compression connection means by gripping the mounting sleeve and axially displacing the mounting sleeve with respect to the outer sleeve against the biasing force of the mounting sleeve spring in the proximal direction to an unlocked position. With the mounting sleeve arranged in the unlocked position, the latch arms are allowed to be deflected in the radial outward direction by the tubular end section of the housing pushing against a ramp on the latch arms upon insertion or removal. The tubular end section of the housing may thus be inserted into and/or removed from the open distal end of the front-end device when the mounting sleeve is in the unlocked position. When the tubular end section has been fully inserted the latch arms are allowed to relax and latch to respective apertures in the tubular end section of the housing. The user can now release the mounting sleeve thus allowing the mounting sleeve spring to translate the mounting sleeve back into the unlocked position. As the tubular end section of the housing is inserted into the open distal end of the front-end device the plunger is inserted into the syringe barrel so as to engage the stopper of the syringe. The latch arms latch to the proximal end of the housing and attach the front-end device to the back-end device. The auto-injector is thus particularly simple and intuitive to assemble before an injection is performed.

Both the back-end device and the front-end device of the auto-injector are designed to be used in a plurality of injections. The only single-use element is the pre-filled syringe that is inserted into the front-end device before assembly of auto-injector. This allows for the reduction of production costs and minimizes waste.

According to yet another possible embodiment of the invention, an interlock switch may be arranged within the back-end device capable of detecting the axial displacement of the needle shroud slidably arranged with respect to the support sleeve and adapted to rest on the skin of a patient receiving an injection. The interlock switch thus detects if the needle shroud is in contact with the skin of the patient and is preferably part of a mechanism that prevents an activation of the motor of the back-end device. The motor of the back-end device may be an electric motor, a spring driven or pneumatic motor or another drive means.

According to yet another possible embodiment of the invention, the back-end device further comprises a sensor unit for detecting actual parameters of the injection, a memory unit for storing user related data and/or specification parameters and a means to provide a visual, acoustical and/or haptic feedback to the user of the auto-injector. The stored user related data may be used for compliance monitoring and thus be used to monitor the frequency of the injections that are the patient performs. In particular when the patient is on a medication, the proper dosage and and/or frequency of the administration may be supervised The sensor unit is capable of detecting actual parameters, like the type of medicament or drug contained in the pre-filled syringe in particular by means of radio frequency identification (RFID) or barcode reading. This allows for, amongst others, an automatic configuration of the auto-injector to properties of the medicament. For example, the penetration depth of the injection needle may be automatically adapted to a depth as required by the medicament. Furthermore, a set of device specification parameters may be stored in the memory unit. The specification parameters stored in the memory unit may be compared with actual parameters determined by the sensor unit during use of the auto-injector. For example, a current measured during the needle insertion process is characterized by the force needed to insert the injection needle into the skin. If the measured current is out of specification, the back-end device detects an incorrect use of the auto-injector and aborts the injection. Another possible application includes comparing the initial position of the stopper with a corresponding specification parameter at the beginning of the injection. If the position of stopper is out of specification, the back-end device detects that a used and empty syringe is loaded to the front-end device and disable the injection mechanism to prevent injuries. The auto-injector may fail to operate when no syringe is inserted into the syringe retainer.

Visual means of the back-end device may in particular comprise a display, preferably a liquid crystal display (LCD), that shows the injection progress, injection completion, historical user data and/or drug properties, like an expiry date. The display may show messages to remind the patient to take his medicament, specification parameters, an operation mode and/or the type of the medicament contained in the pre-filled syringe. Additionally or alternatively, the back-end device may comprise adequate means to provide an acoustic and/or haptic feedback to the patient and/or the user of the auto-injector.

According to yet another possible embodiment of the invention, the back-end device further comprises an encoder sensor capable of determining the position of the plunger. Detection of the position of the plunger may be used to control the translation speed of the plunger. In particular, the translation speed of the plunger may be adapted to the different phases of the drug delivery comprising the needle insertion phase, the expelling of the medicament and the needle retraction phase. In particular, the encoder sensor may be arranged as a rotary or linear encoder capable of detecting the position of the plunger and converting the detected position to a corresponding digital or analogue signal.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIGS. 3A and 3B show two different sectional views of the front-end device during syringe assembly;

FIGS. 4A and 4B show the front-end device of the invention that is connected to the back-end device;

Corresponding parts are marked with the same reference symbols in all figures.

DETAILED DESCRIPTION

Figure 1A:
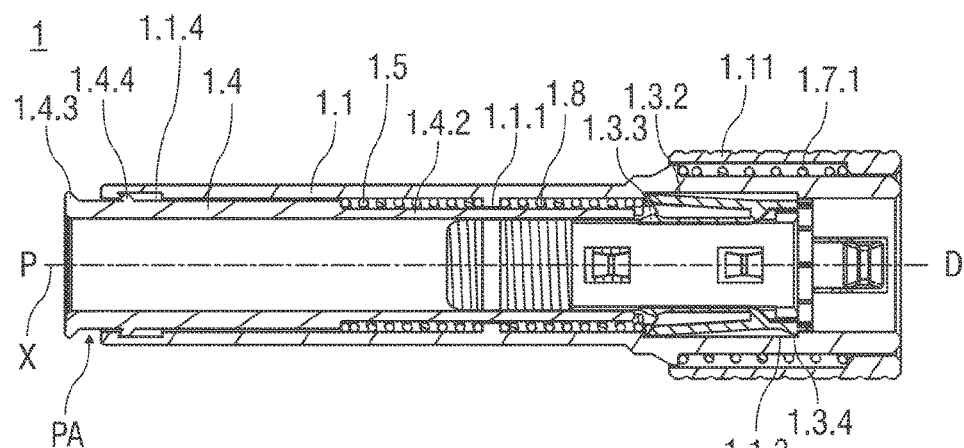
FIGS. 1A and 1B show sectional views of a reusable front-end device before a pre-filled syringe is loaded into the front-end device.
Figure 1B:
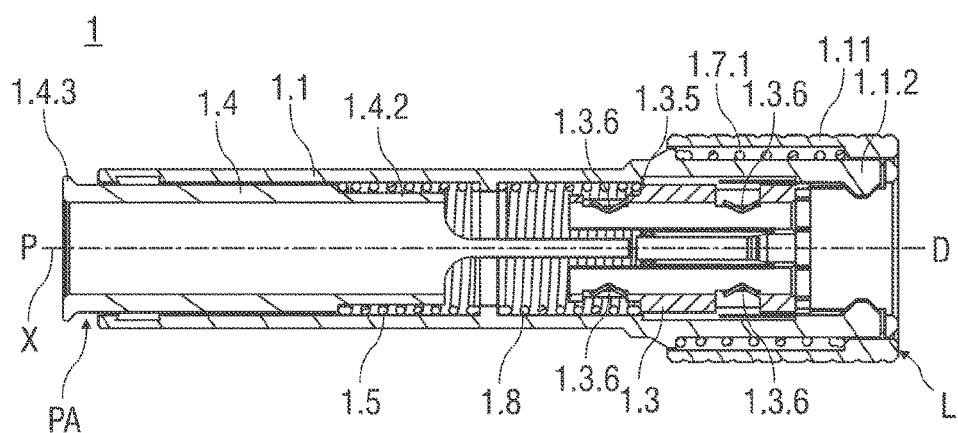

FIGS. 1A and 1B show sectional views of a reusable front-end device 1.

An auto-injector A comprises the substantially cylindrical front-end device 1, the reusable back-end device 3 and a syringe 2 that is insertable into the front-end device 1. The front-end device 1 is attachable to the reusable back-end device 3 via a compression connection means. The back-end device 3 provides the auto-injector A with a variety of features as described herein before. In particular, the back-end device 3 comprises components as described herein before.

FIGS. 1A and 1B show the front-end device 1 before the syringe 2 containing a dose of a liquid medicament is loaded thereto.

The back-end device 3 (shown in FIGS. 6A and 6B) comprises driving means, like an electric motor of the auto-injector A that may be activated to translate the pre-filled syringe 2 within the front-end device 1 parallel to an axis X of the substantially cylindrical front-end device 1 and to expel the medicament contained in the pre-filled syringe 2.

The front-end device 1 comprises a tubular outer sleeve 1.1, a syringe retainer 1.3 adapted to receive the syringe 2, an annular mounting sleeve 1.11 and a substantially cylindrical needle shroud 1.4. The needle shroud 1.4 and the syringe retainer 1.3 are slidably arranged with respect to the outer sleeve 1.1.

An annular projection 1.1.1 is formed to an inner surface of the outer sleeve 1.1 and projects in the radial inward direction. A transfer spring 1.5 bears against the needle shroud 1.4 in the proximal direction P and against the annular projection 1.1.1 in the distal direction D to bias the needle shroud 1.4 in the proximal direction P. The needle shroud 1.4 is located in an advanced position PA and protrudes the outer sleeve 1.1 of the front-end device 1 in the proximal direction P.

At least on but preferably two or more flexible arms 1.3.2 are formed to lateral walls of the syringe retainer 1.3. The flexible arms 1.3.2 are arranged on opposite sides of the syringe retainer 1.3 and latch to the outer sleeve 1.1 to prevent an axial translation of the syringe retainer 1.3 when the pre-filled syringe 2 is loaded therein. The flexible arm 1.3.2 comprises an inner release ramp 1.3.3 that may be engaged by an extension arm 1.4.2 formed to the needle shroud 1.4 and projecting therefrom in the distal direction D. The extension arm 1.4.2 engaging the release ramp 1.3.3 unlatches the flexible arm 1.3.2 and releases the syringe retainer 1.3, so that the syringe retainer 1.3 may be axially displaced in the proximal direction P with respect to the outer sleeve 1.1.

A longitudinal first recess 1.1.3 is formed into an inner surface of a distal section of the outer sleeve 1.1 parallel to a longitudinal axis X. The first recess 1.1.3 accommodates a first catch 1.3.4 formed to an outer surface of the syringe retainer 1.3. The first catch 1.3.4 is retained in first recess 1.1.3 so as to limit the axial displacement of the syringe retainer 1.3 relative to the outer sleeve 1.1 in the distal direction D.

A return spring 1.8 bears proximally against the annular projection 1.1.1 and against a circumferential bearing surface 1.3.5 of the syringe retainer 1.3 in the distal direction D. The return spring 1.8 biases the syringe retainer 1.3 with respect to the outer sleeve 1.1 in the distal direction D.

A radially protruding annular flange 1.4.3 is formed to a proximal end of the needle shroud 1.4. The annular flange 1.4.3 is adapted to rest on the skin of the patient during the injection. A second catch 1.4.4 projects radially outwards from an outer surface of the needle shroud 1.4 and into a second recess 1.1.4 formed into an inner surface of the outer sleeve 1.1. The second catch 1.4.4 travels along the second recess 1.1.4 and limits a maximal axial displacement of the needle shroud 1.4 relative to the outer sleeve 1.1.

The annular mounting sleeve 1.11 encompasses a distal section of the outer sleeve 1.1 and is slidably arranged with respect thereto. A mounting sleeve spring 1.7.1 that is arranged as a compression spring biases the mounting sleeve 1.11 with respect to the outer sleeve 1.1 in the distal direction D towards a locked position L. In the locked position L, the mounting sleeve 1.11 provides a counter bearing for latch arms 1.1.2 shown in FIG. 1B.

At least on but preferably two or more latch arms 1.1.2 are formed to opposite sides of the distal section of the outer sleeve 1.1 that may latch to a housing 3.1 of the back-end device 3 to mount the front-end device 1 thereto. The mounting sleeve 1.11 abuts against the latch arms 1.1.2 in the radial inward direction to prevent an outward deflection of the latch arms 1.1.2. The mounting sleeve 1.11, the mounting sleeve spring 1.7.1 and the latch arms 1.1.2 provide the compression connection means that mounts the front-end device 1 to the back-end device 3 of the auto-injector A.

As best seen in FIG. 1B, a plurality of radially inwards projecting retaining projections 1.3.6 are formed to an inner surface of the syringe retainer 1.3 that are adapted to frictionally engage a barrel 2.3 of the syringe 2.

Figure 2A:
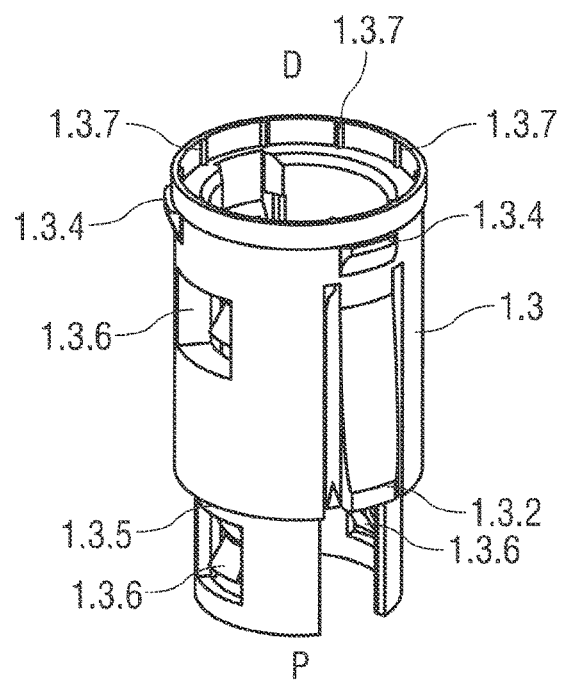
FIGS. 2A and 3B show a syringe retainer in different perspective views.
Figure 2B:
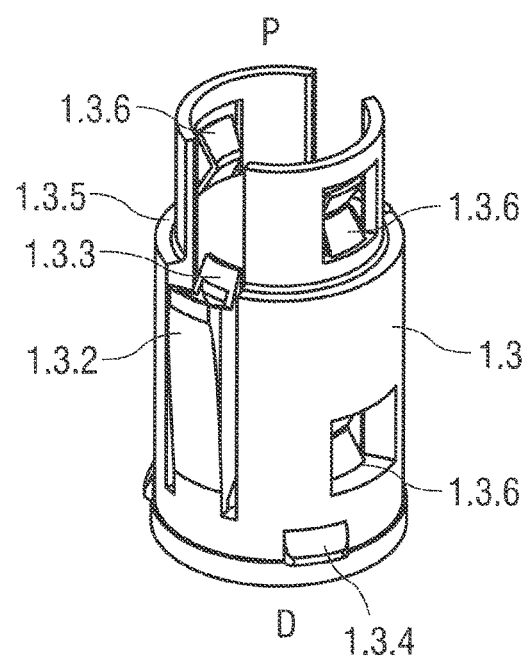

FIGS. 2A and 2B show the syringe retainer 1.3 in different perspective views. The syringe retainer 1.3 features the first catches 1.3.4, the bearing surface 1.3.5, the retaining projections 1.3.6 and the flexible arms 1.3.2 comprising the release ramps 1.3.3. A plurality of friction ribs 1.3.7 is formed to a distal end of the syringe retainer 1.3. The friction rib 1.3.7 protrudes radially inwards and is adapted to frictionally engage a barrel collar 2.3.1 of the syringe 2 and mount the syringe 2 to the syringe retainer 1.3. (As illustrated in FIG. 3B)

Figure 3A:
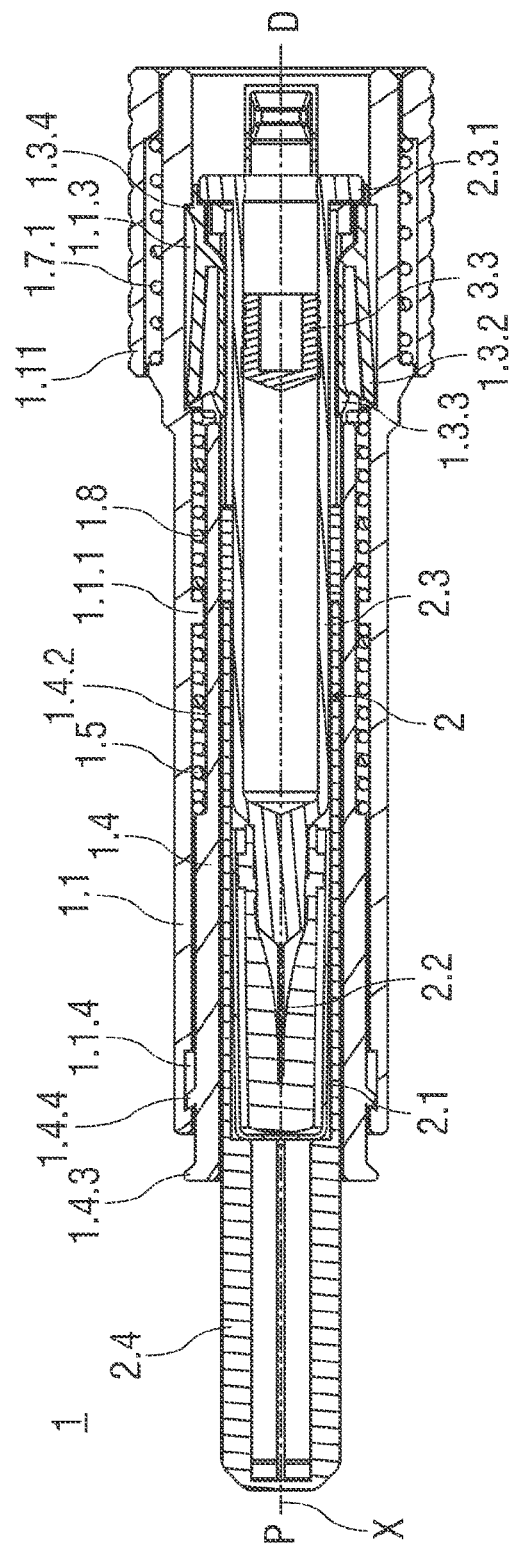
Figure 3B:
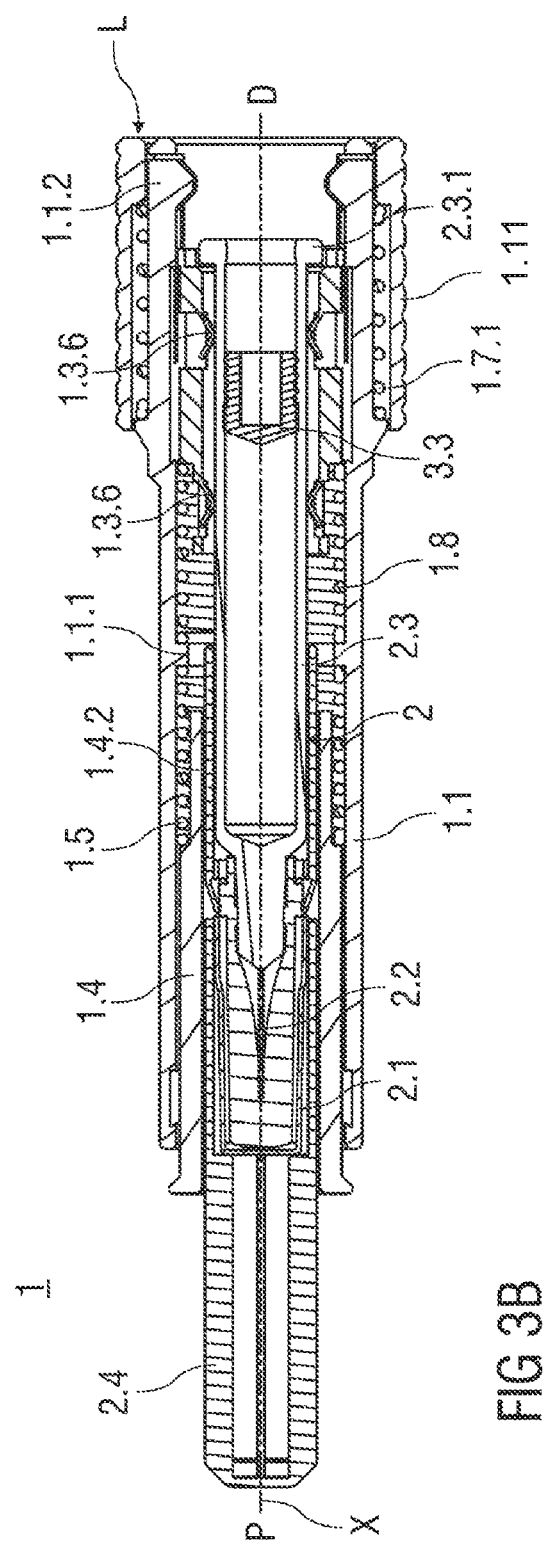

FIGS. 3A and 3B show two different sectional views of the front-end device 1. The pre-filled syringe 2 is inserted into the syringe retainer 1.3 that is retained in a retracted first position I, so that an injection needle 2.2 attached to the proximal tip of the pre-filled syringe 2 is retained within the front-end device 1.

The syringe 2 comprises a stopper 3.3 that liquid tightly seals the barrel 2.3 and is connectable to a plunger 3.2 of the back-end device 3. The stopper 3.3 may be displaced in the proximal direction P to expel the dose of the medicament contained in the barrel 2.3 through the injection needle 2.2 of the pre-filled syringe 2.

The injection needle 2.2 is covered by a needle cap 2.1. Before or after the syringe 2 is inserted into the front end device 1, an elongated tubular cover 2.4 is attached to the proximal end of the syringe 2, snapping on to the needle cap 2.1 by means of snaps (see FIG. 3) and thus retained. The tubular cover 2.4 projects from the proximal end of the front-end device 1 when the syringe 2 is inserted therein. The tubular cover 2.4 may be easily gripped and pulled in the proximal direction P to remove the needle cap 2.1 from the proximal tip of the pre-filled syringe 2.

Alternatively, the needle cap 2.1 and the tubular cover 2.4 may be arranged as one piece.

Figure 4B:
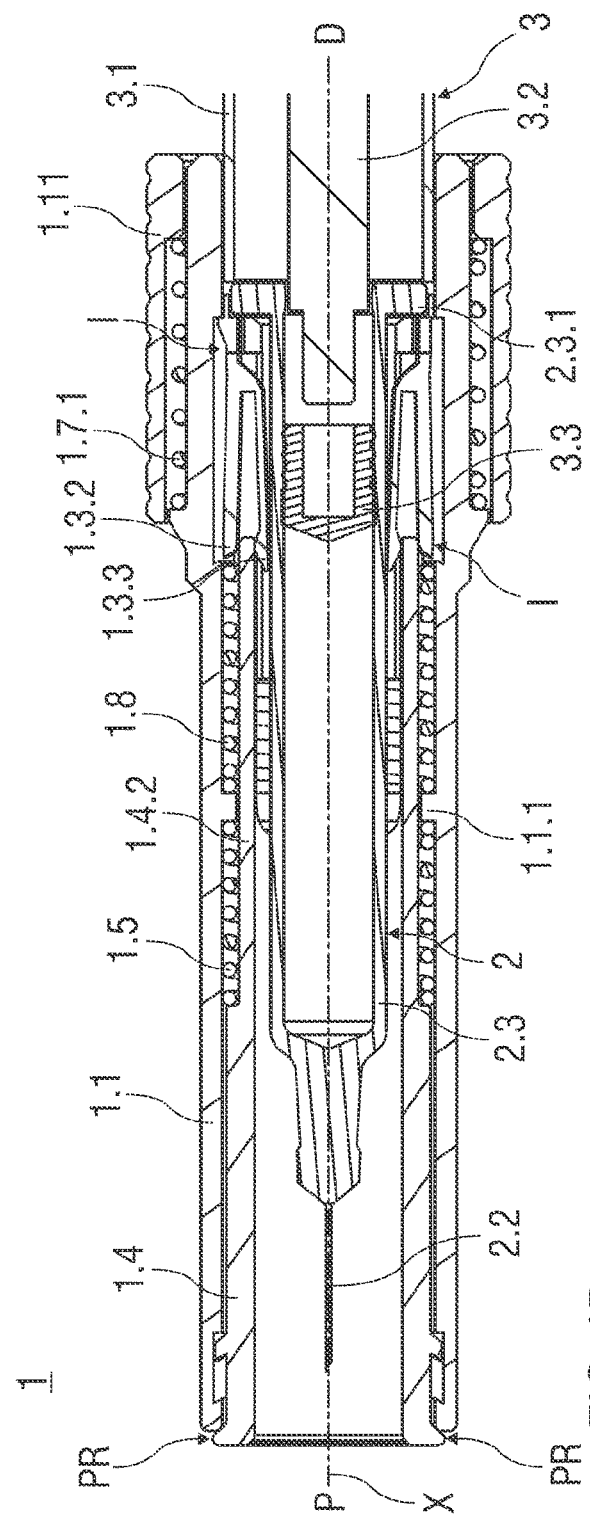

FIGS. 4A and 4B show the front-end device 1 that is connected to the back-end device 3. The tubular cover 2.4 and the needle cap 2.1 has been removed from the pre-filled syringe 2 retained within the front-end device 1 and the injection needle 2.1 is exposed. The front-end device 1 is attached to the back-end device 3 by the latch arms 1.1.2 that latch to a proximal end of a housing 3.1 of the back-end device 3.

The front-end device 1 is attached to or detached from the back-end device 3 by gripping the mounting sleeve 1.11 and axially displacing the mounting sleeve 1.11 with respect to the outer sleeve 1.1 against the biasing force of the mounting sleeve spring 1.7.1 in the proximal direction P to an unlocked position. With the mounting sleeve 1.11 arranged in the unlocked position, the latch arms 1.1.2 are allowed to be deflected in the radial outward direction by the tubular end section of the housing 3.1 pushing against a ramp on the latch arms 1.1.2 upon insertion or removal. The tubular end section of the housing 3.1 may thus be inserted into and/or removed from the open distal end of the front-end device 1 when the mounting collar 1.11 is in the unlocked position. When the tubular end section has been fully inserted the latch arms 1.1.2 are allowed to relax and latch to respective apertures in the tubular end section of the housing 3.1.

When the back-end device 3 is attached to the front-end device 1 the user can release the mounting sleeve 1.11 thus allowing the mounting sleeve spring 1.7.1 to translate the mounting sleeve 1.11 into the locked position. As the tubular end section of the housing 3.1 is inserted into the open distal end of the front-end device 1 the plunger 3.2 is inserted into the barrel 2.3 so as to engage the stopper 3.3 of the syringe 2. The latch arms 1.1.2 latch to the proximal end of the housing 3.1 and attach the front-end device 1 to the back-end device 3. Upon release, the mounting sleeve 1.11 is driven back to the locked position L by the mounting sleeve spring 1.7.1. The mounting sleeve 1.11 in the locked position L abuts against the latch arms 1.1.2 and prevents the latch arms 1.1.2 from deflecting radially outwards thus preventing disengagement of the proximal end of the housing 3.1 from the front end device 1. The auto-injector A is now assembled and ready to be used for an injection delivering the dose of medication to the patient.

The needle shroud 1.4 is pushed against the skin of the patient receiving the injection, whereby the needle shield 1.4 is translated into the outer sleeve 1.1 to a retracted position PR. As best seen in FIG. 4B, the extension arm 1.4.2 engages the release ramp 1.3.3 to deflect the flexible arm 1.3.2 radially inwards, whereby the syringe retainer 1.3 is released from the outer sleeve 1.1 for translation in the proximal direction P. The reusable motor of the back-end device 3 may now be activated to translate the syringe retainer 1.3 and the pre-filled syringe 2 in the proximal direction P.

The needle shroud 1.4 may comprise features that communicate to the back-end device 3 that the needle shroud 1.4 is in contact with the skin of the patient. The back-end device 3 may comprise a mechanism like an interlock switch that allows for an expelling of the dose of the medicament contained in the syringe 2 only if the contact of the needle shroud 1.4 with the skin is detected.

Figure 5A:
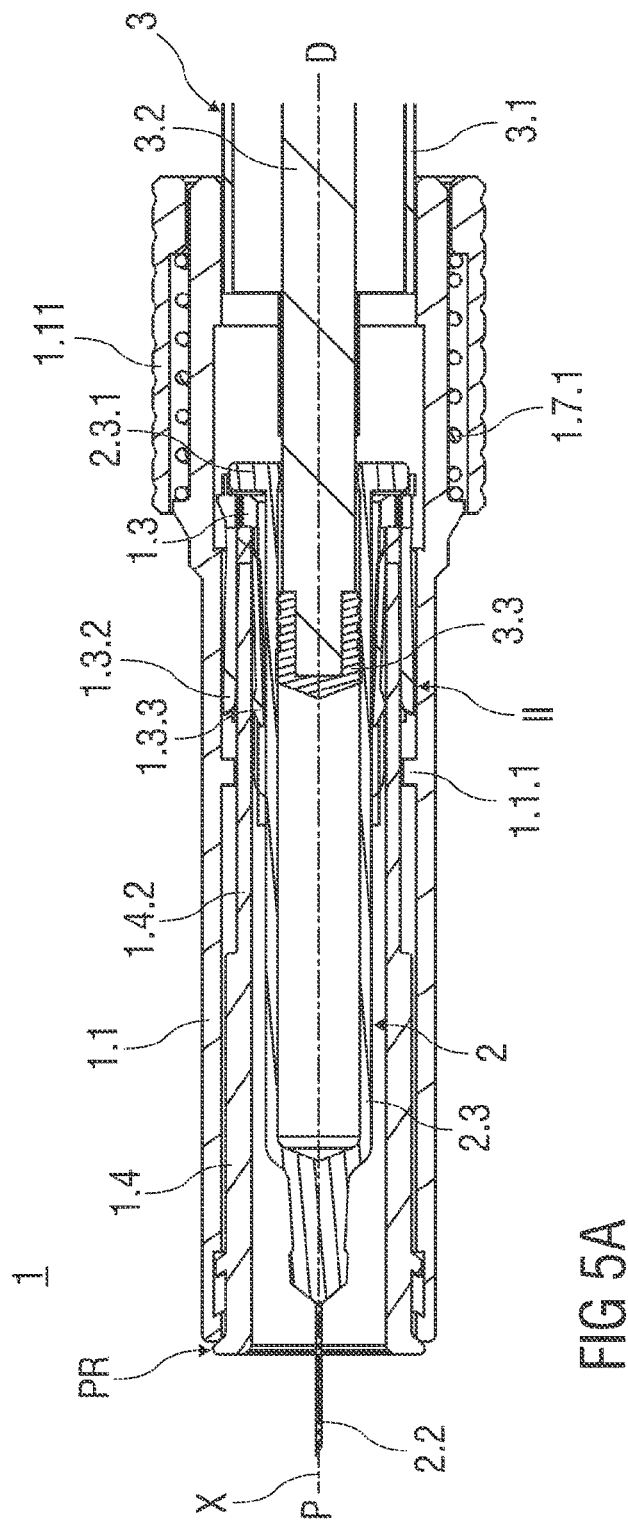
FIGS. 5A and 5B show two sectional views of the front-end device in mid injection; snd
Figure 5B:
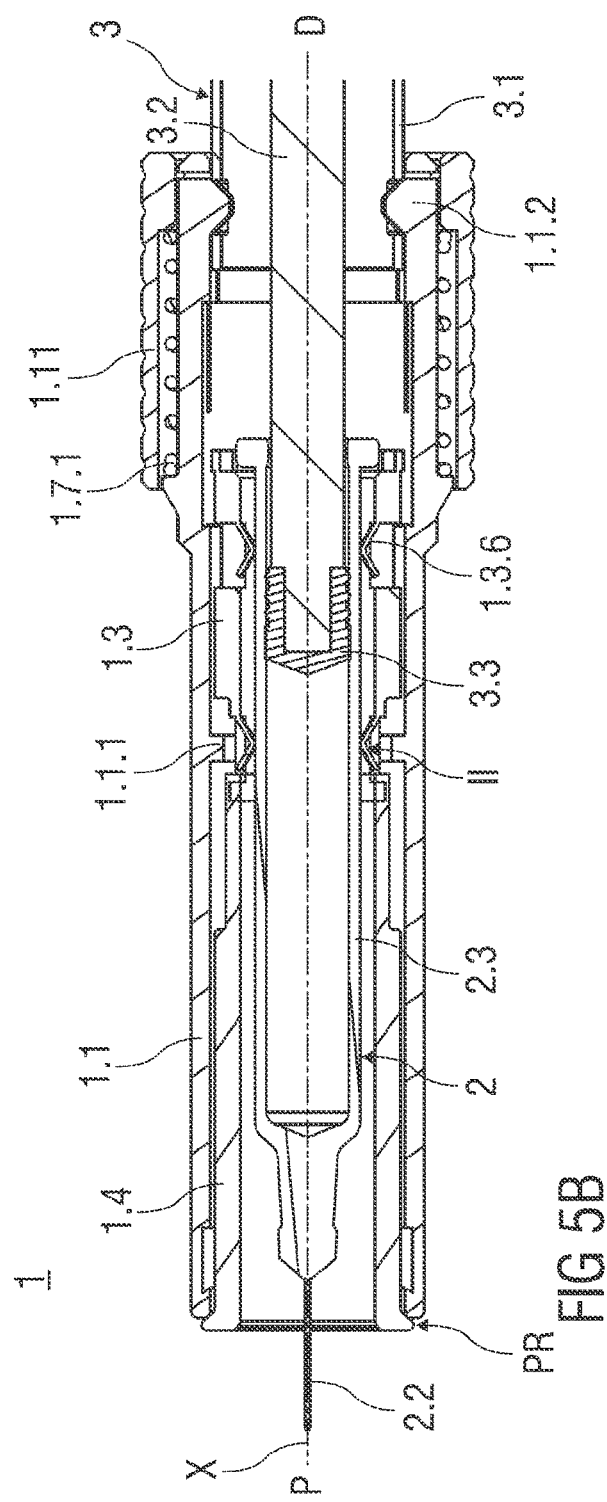

FIGS. 5A and 5B show two sectional views of the front-end device 1 attached to the back end-device 3 in mid injection. The syringe retainer 1.3 holding the syringe 2 is moved proximally to a second position II compressing the return spring 1.8. The injection needle 2.2 protrudes the front-end device 1 in the proximal direction P and is inserted into the skin of the patient. An injection depth may be defined by the length of the compressed return spring 1.8 between the rib 1.1.1 and the syringe retainer 1.3. Alternatively, the needle shroud 1.4 may comprise a stop or rib (not illustrated) that interacts with the syringe retainer 1.4 to limit the penetration depth of the injection needle 2.2.

As the syringe retainer 1.3 has bottomed out the plunger 3.3 connected to the stopper 3.3 is driven by the motor of the back-end device 3 in the proximal direction P to expel the dose of the medicament contained in the syringe 2 through the injection needle 2.2.

After the dose of medication is delivered, the auto-injector A is removed from the injection site allowing the needle shroud 1.4 to advance into the advanced position PA driven by the transfer spring 1.5. This motion can be detected by the back-end device 3, which can then release or actively withdraw the plunger 3.2 allowing retraction of the syringe 2. The syringe retainer 1.3 is returned to the first position I by the action of the relaxing return spring 1.8, whereby the injection needle 2.2 is withdrawn from the skin of the patient and covered inside the needle shroud 1.4 for preventing needle access.

Alternatively or additionally, the motor direction of the motor is reversed to retract the syringe 2 and the syringe retainer 1.3 to the first position I.

As the transfer spring 1.5 relaxes and moves the needle shroud 1.4 back to the advanced position PA, the extension arm 1.4.2 disengages the release ramp 1.3.3. As the syringe retainer 1.3 is back in the first position I the flexible arm 1.3.2 latches to the outer sleeve 1.1 to re-attach the syringe retainer 1.3 to the outer sleeve 1.1. The auto-injector A is disassembled and the back-end device 3 is detached from the front-end device 1. For this purpose the mounting sleeve 1.11 is gripped and axially displaced with respect to the outer sleeve 1.1 against the biasing force of the mounting sleeve spring 1.7.1 in the proximal direction P to the unlocked position. With the mounting sleeve 1.11 arranged in the unlocked position, the latch arms 1.1.2 are allowed to be deflected in the radial outward direction by the tubular end section of the housing 3.1 pushing against a ramp on the latch arms 1.1.2 when pulled away from the re-usable front end 1. The tubular end section of the housing 3.1 may thus be removed from the open distal end of the front-end device 1 when the mounting collar 1.11 is in the unlocked position. When the tubular end section has been removed the latch arms 1.1.2 are allowed to relax. The mounting sleeve 1.11 returns to the locked position when released. The tubular cover 2.4 holding the needle cap 2.1 is re-inserted into the open proximal end of the front-end device 1, so that the injection needle 2.2 is covered by the needle cap 2.1. The tubular cover 2.4 is pushed into the front-end device 1 to detach the syringe 2 from the syringe retainer 1.3. The empty syringe 2 may then be removed from the front-end device 1 and disposed. Alternatively, the whole front-end device 1 may be disposed of to reduce the risk of cross contamination.

Figure 6A:
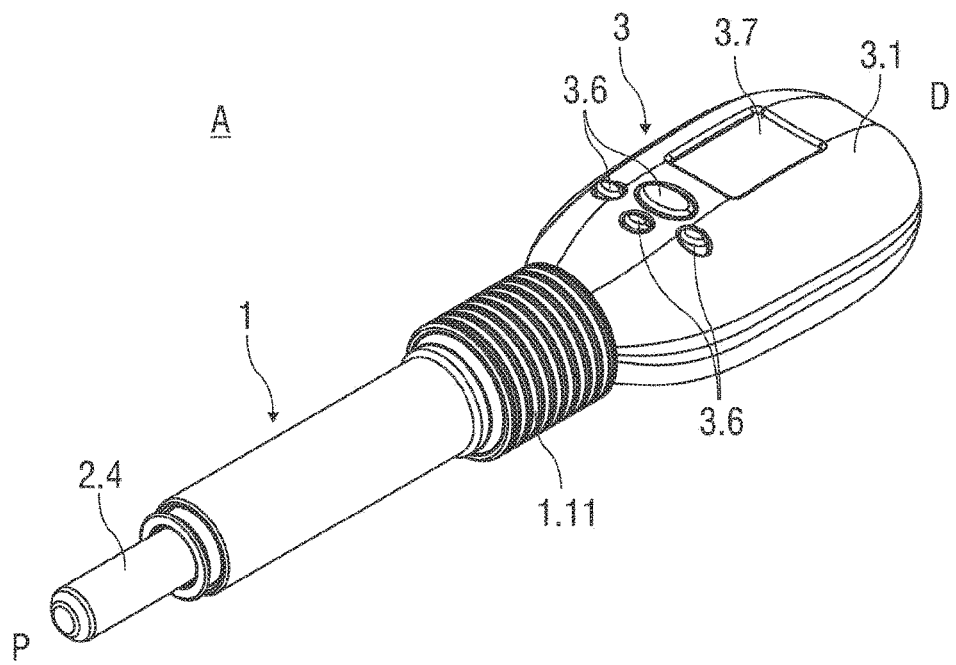
FIGS. 6A and 6B show the assembled auto-injector comprising the back end-device 3 and the front-end device in a perspective and a sectional view.
Figure 6B:
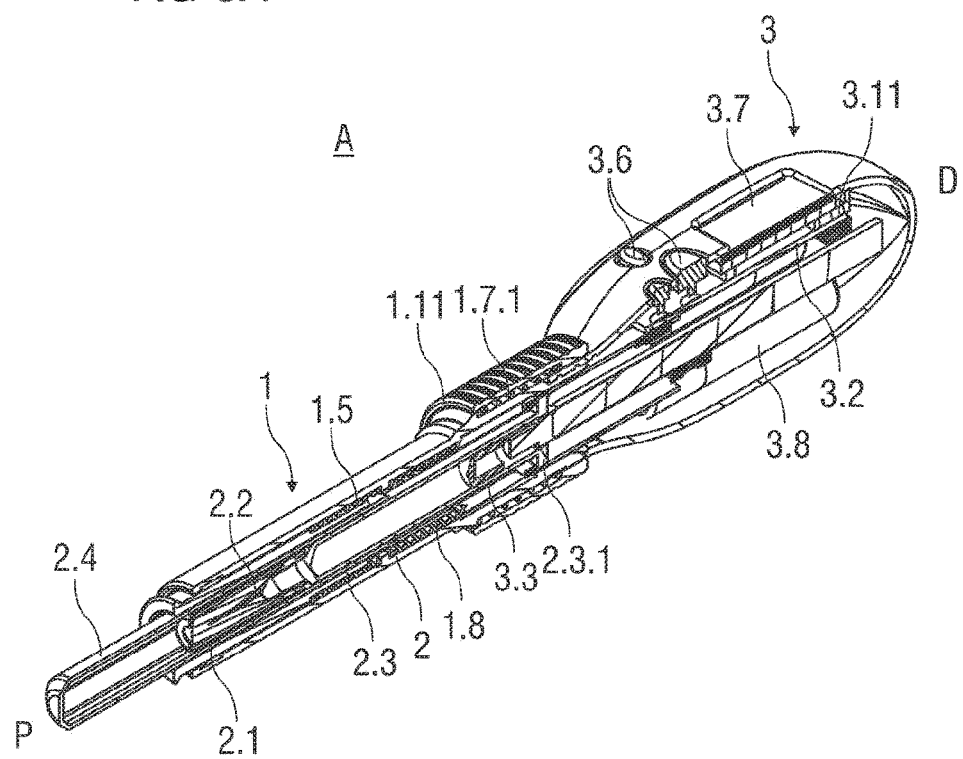

FIGS. 6A and 6B show the assembled auto-injector A comprising the back end-device 3 and the front-end device 1 in a perspective and a sectional view. The back-end device 3 and the front-end device 1 are attached to each other by the compression connection means comprising the mounting sleeve 1.11, the mounting sleeve spring 1.7.1 and the latch arms 1.1.2 engaging the proximal end of the housing 3.1.

The housing 3.1 of the back-end device 3 comprises substantially oval cross-sections of different dimensions.

The reusable back-end device 3 of the auto-injector A comprises a plurality of control elements 3.6 used to activate and control a variety of features of the auto-injector A, such as activating and de-activating the electric motor that axially translates the plunger 3.2 to insert and/or retract the injection needle 2.2 and to inject the dose of the medicament. Furthermore, the speed of the needle insertion or the penetration depth of the injection needle 2.2 may be controlled and/or time delays may be introduced by the user. The back-end device 3 may be provided with a variety of user-selectable speed profiles that control the torque provided by the motor to facilitate the needle insertion process and/or to modify the injection speed. Various parameters may be modified to suit the user and/or to drug requirements, like the viscosity of the medication.

The back-end device 3 may comprise a memory unit (not illustrated) that may be used to store user related data for compliance monitoring. If the patient is on a medication, the back-end device 3 can be used to monitor that the dose of the medicament is administered at correct regular intervals. Furthermore, a set of device specification parameters may be stored in the memory unit. The specification parameters may be compared with actual parameters determined during use of the auto-injector A. For example, the force needed to insert the injection needle 2.2 into the skin is characterized by the current measured during the needle insertion process. If the measured current is out of specification, the back-end device 3 detects an incorrect use of the auto-injector A and may abort the injection. Another possible application includes comparing the initial position of the stopper 3.3 with a corresponding specification parameter at the beginning of the injection. If the position of stopper 3.3 is out of specification, the back-end device 3 detects that a used and empty syringe 2 is loaded to the front-end device 1 and may disable the injection mechanism to prevent injuries. The auto-injector A may fail to operate when no syringe 2 is inserted into the syringe retainer 1.3.

The back-end device 3 has a display 3.7, preferably a liquid crystal display (LCD), that may visually display injection progress, injection completion, historical user data and/or drug properties, like an expiry date. The display 3.7 may display messages to remind the patient to take his medicament, specification parameters, an operation mode and/or the type of the medicament contained in the pre-filled syringe 2. Additionally or alternatively, the back-end device 3 may comprise adequate means to provide an acoustic and/or haptic feedback to the patient and/or the user of the auto-injector A.

The back-end device 3 may comprise a sensor unit (not illustrated) capable of detecting actual parameters, like the type of medicament or drug contained in the pre-filled syringe 2 in particular by means of radio frequency identification (RFID) or barcode reading. This allows for an automatic configuration of the auto-injector A to properties of the medicament. For example, the penetration depth of the injection needle 2.2 may be automatically adapted to a depth as required by the medicament. The auto-injector A is particularly suited to be used for administering a variety of drugs that may require an intradermal, a transcutaneous or an intramuscular injection.

Additional sensor units (not illustrated) may be arranged in particular as micro switches that detect the correct assembly of the auto-injector A and/or the correct mounting of the front-end device 1 to the back-end device 3. The sensor units may also be arranged as encoders, light gates and/or current monitoring systems.

The motor of the auto-injector A is powered by an energy supply 3.8 that may be provided by a set of rechargeable or disposable batteries. The torque provided by the motor is transferred to the plunger 3.2 by a gearbox 3.9.1 comprising a plurality of gearwheels 3.9.1 and a worm gear 3.2.1 A plurality of gear teeth 3.2.1 are formed to the plunger 3.2 that are engaged by one of the gearwheels 3.9.1 to convert the rotational motion to a linear motion of the plunger 3.2 as in a rack and pinion gear pair. The gearbox in particular increases the output torque transferred to the plunger 3.2 to deliver the required plunger motion and force.

Alternative back-end devices 3 may be arranged without a gearbox. Other forms of gearboxes may likewise be applied—eg a lead screw driven directly or indirectly by the motor.

A distal displacement of an interlock connected to the needle shroud 1.4 may be detected by the interlock switch 3.10. The detected distal position PA, PR of the needle shroud 1.4 indicates whether or not the auto-injector A is correctly placed onto the skin of the patient so that the dose of medication may be injected. The back-end device 3 may be programmed in a manner that allows for an activation of the motor only if the needle shroud 1.4 is in contact with the skin of the patient. Furthermore, the direction of the motor may be immediately inverted when the auto-injector A is removed from the injection site at any time of the injection allowing for a partial delivery of the dose of the medicament. Upon removal of the auto-injector A from the injection site, the injection needle 2.2 is retracted to reduce the risk of an accidental needle stick. Removal from the injection site may be detected by the needle shroud 1.4 returning into the advanced position PA.

An electronic control unit 3.11 is arranged within the housing 3.1 that controls the various features of back-end device 3 and in particular the motor The electronic control unit 3.11 may comprise a printed circuit board (PCB). A closed loop motion control may be embedded in the electronic control unit 3.11 that controls the speed of the motor to reduce shock loads on the reusable auto-injector A and/or on the syringe 2 and hence reduce the risk of breaking the syringe 2.

The electronic control unit 3.11 is capable of detecting a stall of the motor at the end of the injection stroke delivering the dose of medication to the patient. This indicates that the syringe 2 is completely empty and may trigger the needle retraction mechanism of the auto-injector A.

An encoder sensor capable of determining the position of the plunger 3.2 is connected to the gearbox Detection of the position of the plunger 3.2 is used to achieve a phased motion of the plunger 3.2 during the injection. Hence, the translation speed of the plunger 3.2 may be adapted to the different phases of the drug delivery comprising the needle insertion phase, the expelling of the medicament and the needle retraction phase. Needle insertion is thought to be less painfull to the patient when performed quickly whereas injection is considered less painfull when performed rather slowly.

Although the back-end device 3 in the above described embodiment is motor driven, the above described front-end device 1 may likewise be combined with back-end devices having different thrust means such as a compression spring, a torsion spring, a gas spring or a combustion engine.

The above described back-end device 3 may likewise be combined with a disposable front-end device which is completely discarded after use. Although the re-usable front-end device 1 requires fewer resources and produces less waste, the disposable front-end device avoids the risk of cross contamination since none of its components will get in contact with more than one patient.

The invention claimed is:

1. A front-end device of an auto-injector (A) for administering a dose of a liquid medicament, wherein the front-end device is adapted to receive a syringe with an injection needle and a barrel containing the dose of the medicament and comprises
    a tubular outer sleeve,
    a compression connector for attaching the front-end device to a back-end device of the auto-injector (A), wherein the compression connector comprises:
        an annular mounting sleeve that is axially displaceable parallel to a longitudinal axis (X) between a locked position (L) and an unlocked position,
        a mounting sleeve spring biasing the mounting sleeve towards the locked position (L),
        at least one latch arm connected to the back-end device, wherein the at least one latch arm is deflectable in a radial direction, wherein the mounting sleeve in the locked position (L) is arranged to prevent a radial deflection of the at least one latch arm and wherein, in response to axially displacing the annular mounting sleeve to the unlocked position, the mounting sleeve in the unlocked position allows for the radial deflection of the latch arm, so as to allow the latch arm to be deflected on assembly or disassembly of the front-end device to the back-end device and to latch to or unlatch from the front-end device; and
    wherein the compression connector is configured to transition from the locked position (L) to the unlocked position when the annular mounting sleeve is displaced with respect to the tubular outer sleeve against a biasing force of the mounting sleeve spring in a proximal direction to the locked position (L).

2. The front-end device according to claim 1, wherein a syringe retainer adapted to receive the pre-filled syringe is slidably arranged with respect to the outer sleeve, wherein the syringe retainer is arranged to be translated between a first position (I) and a second position (II) and wherein the syringe retainer comprises at least one flexible arm arranged to latch to the outer sleeve to releasably retain the syringe retainer in the first position (I).

3. The front-end device according to claim 2, wherein a needle shroud adapted to rest on a skin of a patient is slidably arranged with respect to the outer sleeve, wherein the needle shroud is arranged to be translated between an advanced position (PA) and a retracted position (PR) and wherein the needle shroud comprises an extension arm that is arranged to engage a release ramp on the syringe retainer to de-latch the syringe retainer from the outer sleeve in the retracted position (PR).

4. An auto-injector (A) for administering a dose of a liquid medicament, comprising:
    a front-end device; and
    a reusable back-end device comprising:
        a housing,
        a plunger connected to or adapted to engage a stopper providing a fluid tight seal for a distal end of the barrel,
        a motor for displacing the plunger connected to the stopper; and a compression connector for attaching the front-end device to the back-end device, the compression connector comprising:
            an annular mounting sleeve that is axially displaceable parallel to a longitudinal axis (X) between a locked position (L) and an unlocked position,
            a mounting sleeve spring biasing the mounting sleeve towards the locked position (L),
            at least one latch arm connected to the back-end device, wherein the at least one latch arm is deflectable in a radial direction, wherein the mounting sleeve in the locked position (L) is arranged to prevent a radial deflection of the at least one latch arm and wherein, in response to axially displacing the annular mounting sleeve to the unlocked position, the mounting sleeve in the unlocked position allows for the radial deflection of the latch arm, so as to allow the latch arm to be deflected on assembly or disassembly of the front-end device to the back-end device and to latch to or unlatch from the front-end device; and
        wherein the compression connector is configured to transition from the locked position (L) to the unlocked position when the annular mounting sleeve is displaced with respect to a tubular outer sleeve against a biasing force of the mounting sleeve spring in a proximal direction to the locked position (L).

5. The auto-injector (A) according to claim 4, wherein a tubular cover is connected to a needle cap covering the injection needle of a syringe, wherein the tubular cover is arranged to facilitate removal of the needle cap when the syringe is retained within the front-end device.

6. The auto-injector (A) according to claim 4, wherein a needle shroud adapted to rest on a skin of a patient is slidably arranged with respect to the outer sleeve, wherein the needle shroud is arranged to be translated between an advanced position (PA) and a retracted position (PR), wherein an interlock switch is arranged to detect the position (PA, PR) of the needle shroud.

7. The auto-injector (A) according to claim 4, wherein the back-end device comprises a sensor unit for detecting actual parameters of the injection, a memory unit for storing user related data and/or specification parameters and a feedback provider to a user of the auto-injector (A).

8. The auto-injector (A) according to claim 4, wherein the back-end device further comprises an encoder sensor capable of determining a position of the plunger.

9. The auto-injector (A) according to claim 4, wherein at least one radially inwards projecting retaining projection is formed to an inner surface of a syringe retainer, the retaining projection adapted to frictionally engage the barrel of a syringe.

* * * * *